(12) United States Patent
Furuya et al.

(10) Patent No.: US 6,762,340 B2
(45) Date of Patent: Jul. 13, 2004

(54) ABSORBENT ARTICLE WITH SURFACE STRUCTURAL BODY OF CONTINUOUS FILAMENTS

(75) Inventors: Kodai Furuya, Kagawa (JP); Hiroo Hayashi, Kagawa (JP); Takamitsu Igaue, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 84 days.

(21) Appl. No.: 09/935,406

(22) Filed: Aug. 23, 2001

(65) Prior Publication Data

US 2002/0029025 A1 Mar. 7, 2002

(30) Foreign Application Priority Data

Sep. 1, 2000 (JP) ........................................ 2000-265519

(51) Int. Cl.[7] ................................................ A61F 13/15
(52) U.S. Cl. ........................................ 604/378; 604/384
(58) Field of Search ................................ 604/378, 379, 604/384

(56) References Cited

U.S. PATENT DOCUMENTS 3,949,130 A * 4/1976 Sabee et al. ................ 428/192
5,492,751 A * 2/1996 Butt et al. ................... 428/198
5,695,487 A * 12/1997 Cohen et al. ................ 604/384
5,752,945 A * 5/1998 Mosley et al. .............. 604/370
5,997,989 A * 12/1999 Gessner et al. ............. 428/152
6,245,961 B1 * 6/2001 Roxendal et al. ........... 604/367
6,417,427 B1 * 7/2002 Roxendal et al. ........... 604/378
6,488,670 B1 * 12/2002 Schild et al. .......... 604/385.24

FOREIGN PATENT DOCUMENTS

JP          09-322908         12/1997
JP          09-322909         12/2000

* cited by examiner

*Primary Examiner*—Weilun Lo
*Assistant Examiner*—Jamisue A. Webb
(74) *Attorney, Agent, or Firm*—Darby & Darby (57) ABSTRACT

Disclosed is an absorbent article including: a liquid permeable surface structural body; a backing sheet; an absorbent core disposed between the surface structural body and the backing sheet. The surface structural body is formed by stacking bundles of continuous filaments into at least two layers and partially fixing the continuous filaments of the respective layers together. The individual continuous filaments extend over the entire length of the respective layers. The layers include: a lower layer positioned adjacent to the absorbent layer; and an upper layer positioned away from the absorbent layer and having a smaller width than that of the lower layer. The upper layer is located exclusively at a center portion or laterally opposite side portions of the lower layer.

4 Claims, 5 Drawing Sheets

ABSORBENT ARTICLE WITH SURFACE STRUCTURAL BODY OF CONTINUOUS FILAMENTS

BACKGROUND OF THE INVENTION

1. Field of the Invention

The present invention relates to an absorbent article, such as disposable diaper, sanitary napkin or the like, with a surface structural body of continuous filaments.

2. Description of the Related Art

The conventional absorbent article, such as disposable diaper, sanitary napkin or the like, has a liquid impermeable backing sheet on back side of an absorbent core, and a liquid permeable surface sheet on surface side as liquid receiving side.

The surface sheet of the conventional absorbent article is formed of a liquid permeable non-woven fabric, a synthetic resin film formed with a large number of pores or through holes. However, since the conventional surface sheet has a uniform thickness in a width direction, it is difficult to appropriately fit on the discharge region of a wearer. This results in that a gap is formed between the discharge region and the surface sheet to possibly cause lateral leakage of discharged liquid along the surface sheet.

Therefore, for example, in Japanese Unexamined Patent Publication No. Heisei 9-322908, there has been disclosed an absorbent article in which a liquid permeable surface layer is deformed and bulged toward a wearer at the center portion thereof to form a projecting ridge (bank) for fitting on the discharge region of a wearer.

On the other hand, for preventing lateral leakage of liquid along the foregoing surface layer, there is an absorbent article in which leakage preventing walls extending in longitudinal direction are formed on laterally opposite side portions of the surface sheet. The leakage preventing wall is formed with a hydrophobic sheet raising from the surface sheet and an elastic member provided at the top portion of the hydrophobic sheet. The hydrophobic sheet is raised from the surface sheet by elastic contraction force of the elastic member.

However, in the absorbent article disclosed in Japanese Unexamined Patent Publication No. Heisei 9-322908, since the surface layer is deformed and bulged at the center portion thereof for providing a projecting portion at the center portion of the absorbent article, the structure of the surface layer becomes quite complicate to cause high manufacturing cost.

On the other hand, in case of the absorbent article having the leakage preventing walls, there is required manufacturing process to join the hydrophobic sheet with the surface sheet and to join the elastic member to the hydrophobic sheet. Such additional process steps inherently limit lowering of manufacturing cost.

SUMMARY OF THE INVENTION

The present invention has been worked out in view of the shortcoming in the prior art as set forth above. It is therefore an object of the present invention to provide an absorbent article, in which a bulged portion to be fitted to discharge region of a wearer or laterally opposite banks for preventing leakage of liquid can be manufactured through quite simple process, and which can provide soft contact feeling to the wearer's skin.

According to the present invention, there is provided an absorbent article comprising:

a liquid permeable surface structural body;

a backing sheet;

an absorbent core disposed between the surface structural body and the backing sheet, the surface structural body being formed by stacking bundles of continuous filaments into at least two layers and partially fixing the continuous filaments of the respective layers together, the individual continuous filaments extending over the entire length of the respective layers, wherein the layers include: a lower layer positioned adjacent to the absorbent layer; and an upper layer positioned away from the absorbent layer and having a smaller width than that of the lower layer, and the upper layer is located exclusively at a center portion or laterally opposite side portions of the lower layer.

Preferably, the lower layer has higher hydrophilicity than the upper layer. In this case, the upper layer may be formed of hydrophobic continuous filaments not subjected to hydrophilic treatment, and the lower layer may be formed of hydrophobic continuous filaments treated to be hydrophilic or of hydrophilic continuous filaments.

Also preferably, filament density of the upper layer is different from filament density of the lower layer. In this case, more preferably, filament density of the lower layer is higher than filament density of the upper layer.

The surface structural body may further comprise an intermediate layer of the continuous filaments between the lower layer and the upper layer, and widths of the lower layer, the intermediate layer and the upper layer may be varied in descending order from the lower layer to the upper layer. In this case, hydrophilicities of the upper layer, the intermediate layer and the lower layer may be varied in ascending order from the upper layer to the lower layer. For example, the upper layer may be formed of hydrophobic continuous filaments not subjected to hydrophilic treatment. Alternatively, the lower layer, the intermediate layer and the upper layer may have mutually different filament densities. In this case, preferably, filament densities of the lower layer, the intermediate layer and the upper layer are varied in ascending order from the upper layer to the lower layer.

The upper layer may be located exclusively at laterally opposite side portions of the lower layer, and the upper layer may be water repellent.

In the present invention, since the surface structural body is formed of the continuous filaments to have low density and high bulkiness, it provides soft contact feeling to the skin of a wearer. Especially since the continuous filaments extend over the entire length of the respective layers of the surface structural body, no fiber end appears on the surface thereof. Therefore, the surface of surface structural body is so smooth.

In the surface structural body formed of the continuous filaments, by providing a difference in hydrophilicity and/or filament density between the upper and lower layers, liquid permeability and effect of preventing the liquid from flowing back can be enhanced.

The surface structural body having a difference in hydrophilicity and/or filament density between layers can be manufactured quite simply by continuously feeding continuous filaments of different hydrophilicities and/or filament densities and partially fixing the continuous filaments.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
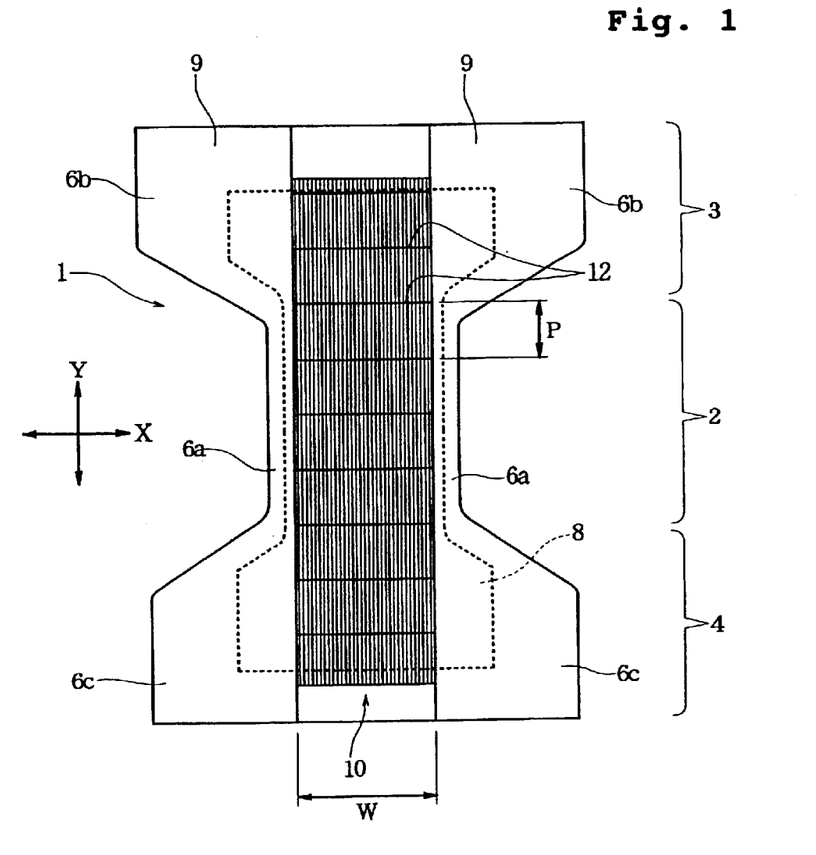
FIG. 1 is a plan view of a disposable diaper as an absorbent article according to a first embodiment of the invention, as viewed from a liquid receiving side.
Figure 2:
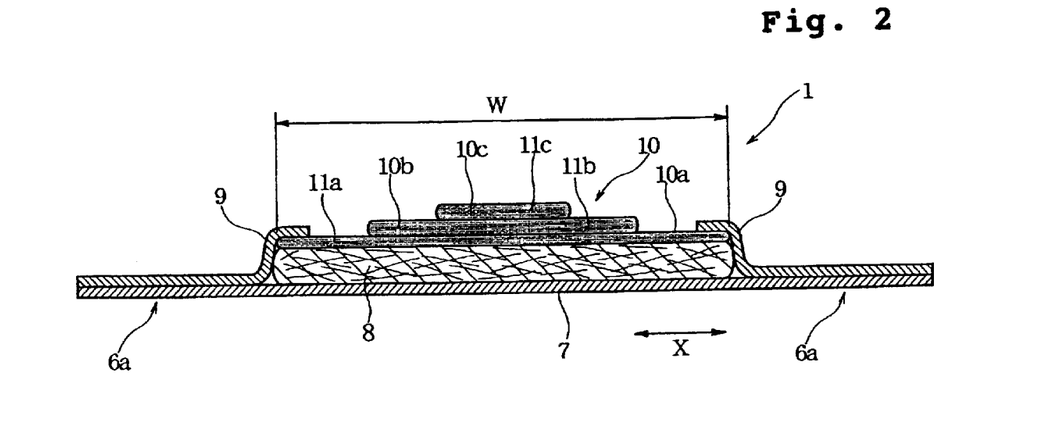
FIG. 2 is a section showing the disposable diaper shown in FIG. 1.
Figure 3:
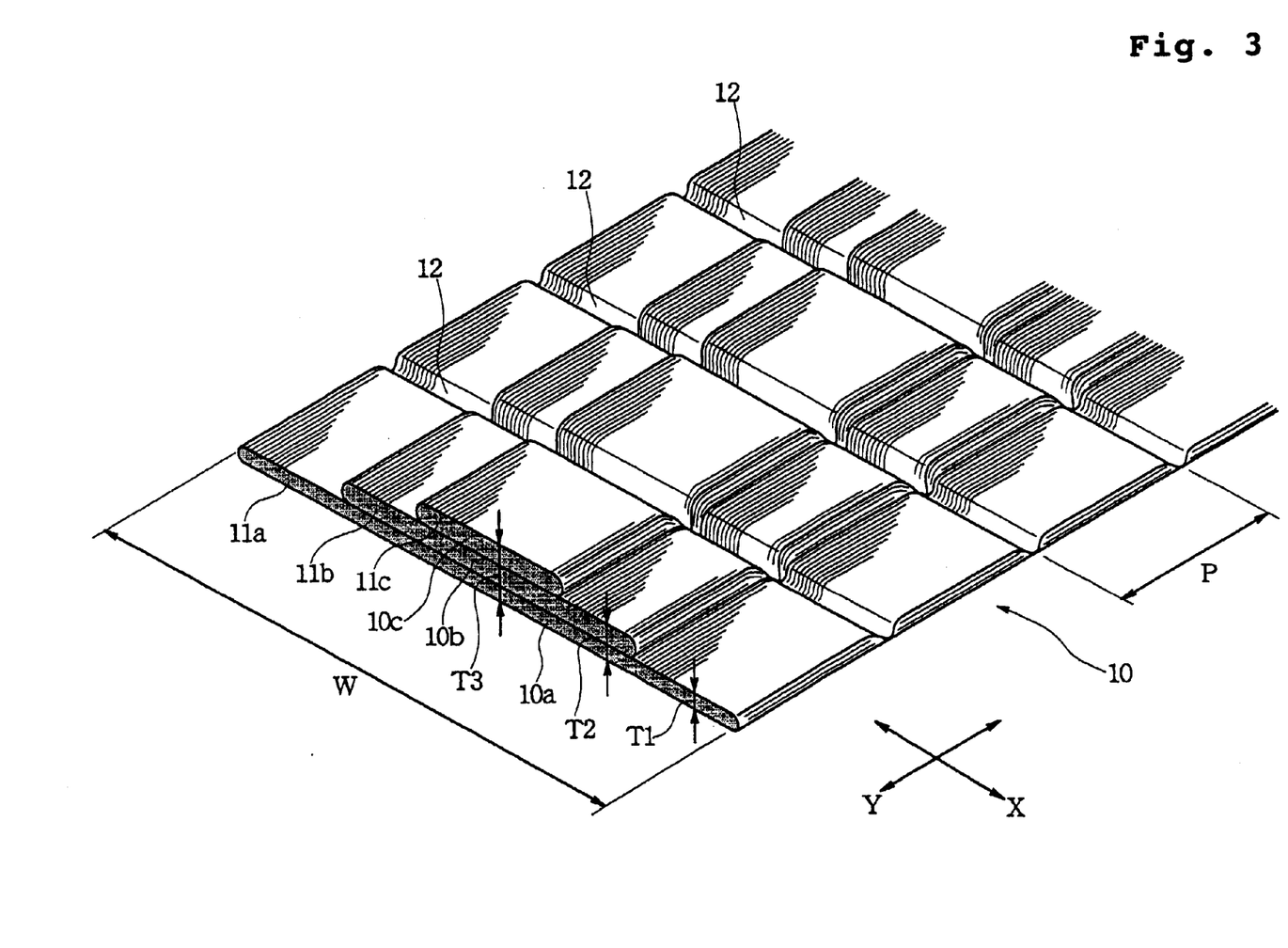
FIG. 3 is a partial perspective view of a surf ace structural body to be used in the disposable diaper shown in FIG. 2.
Figure 4:
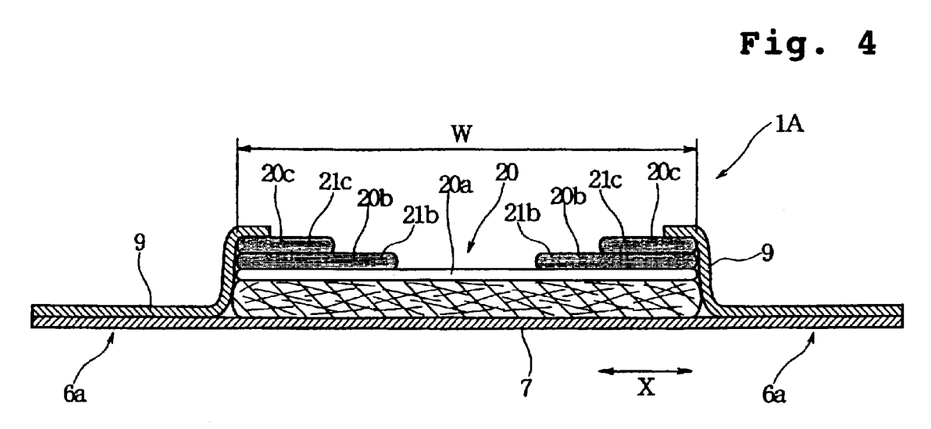
FIG. 4 is a section of a disposable diaper as an absorbent article according to a second embodiment of the invention.
Figure 5:
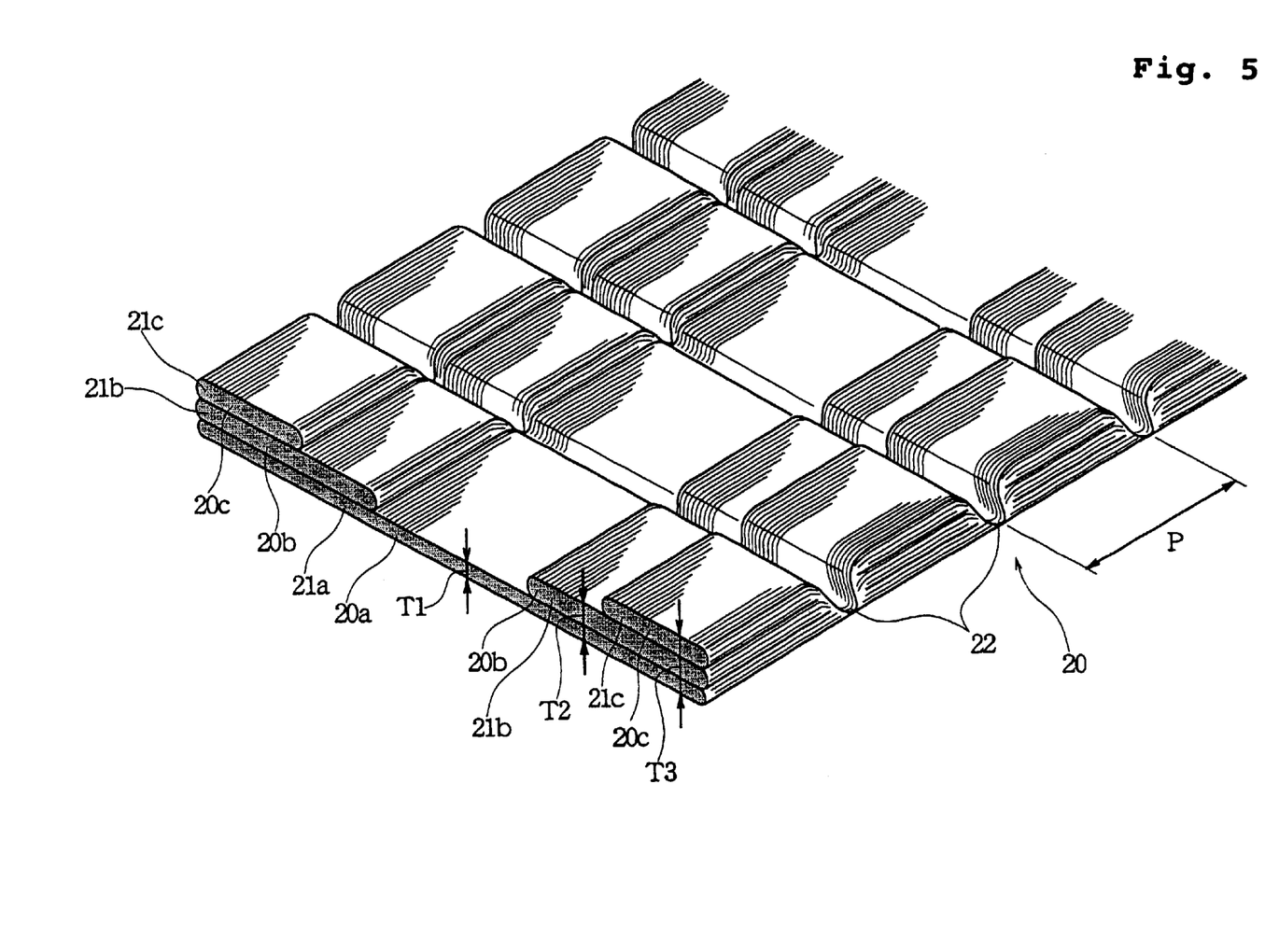
FIG. 5 is a partial perspective view of a surface structural body to be used in the disposable diaper shown in FIG. 4.

FIG. 1 is a plan view of a disposable diaper as an absorbent article according to a first embodiment of the invention, as viewed from a liquid receiving side; FIG. 2 is a section showing the disposable diaper shown in FIG. 1; FIG. 3 is a partial perspective view of a surface structural body to be used in the disposable diaper shown in FIG. 2; FIG. 4 is a section of a disposable diaper as an absorbent article according to a second embodiment of the invention; FIG. 5 is a partial perspective view of a surface structural body to be used in the disposable diaper shown in FIG. 4.

FIG. 1 is a plan view of a disposable diaper 1 in developed form, in which a width direction (lateral direction) is defined as X direction and a longitudinal direction is defined as Y direction. The disposable diaper 1 is of an hourglass shape with an intermediate portion 2 to be applied to a crotch portion of a wearer, a front portion 3 to be applied to an abdominal portion of a wearer and a rear portion 4 to be applied to a hip portion of a wearer.

In the disposable diaper 1, as shown in the section of FIG. 2, an absorbent core (absorbent layer) 8 is laid on a liquid impermeable backing sheet 7. As shown in FIG. 1, the absorbent core 8 is of an hourglass shape dimensioned to extend in the longitudinal direction from a midway position of the front portion 3, through the intermediate portion 2, to a midway position of the rear portion 4. On a liquid receiving side surface of the absorbent core 8, there is laid a liquid permeable surface structural body 10 which is formed of continuous filaments.

As shown in FIG. 2, liquid impermeable side sheets 9 and 9 are joined to laterally opposite sides of the surface structural body 10, respectively. These side sheets 9 and 9 are extended to flap portions 6a and 6a on laterally opposite sides of the intermediate portion 2, flap portions 6b and 6b on laterally opposite sides of the front portions 3, and flap portions 6c and 6c on laterally opposite sides of the rear portion 4, respectively. In each flap portion, the backing sheet 7 and the side sheet 9 are joined by a hot melt type adhesive or the like.

The backing sheet 7 is impermeable to liquid, and is formed of a moisture permeable resin film, a non-woven fabric, a laminate of a resin film and a non-woven fabric, or the like. The absorbent core 8 is formed of a mixture of crushed pulp and SAP (superabsorbent polymer) wrapped with a liquid permeable paper, air laid pulp formed into a sheet by a binder process, an absorbing paper, a non-woven fabric containing hydrophilic fibers as primary component, or the like.

The side sheet 9 is formed of a non-woven fabric such as a through air bonded non-woven fabric, a point bonded non-woven fabric, a spun bonded non-woven fabric, a spun laced non-woven fabric, a melt blown non-woven fabric, an air laid non-woven fabric or the like. Preferably, the side sheet 9 is hydrophobic or water repellent.

As shown in FIGS. 2 and 3, the surface structural body 10 is consisted of three layers including a lower layer 10a adjacent to the absorbent core 8, an intermediate layer 10b on the lower layer 10a and an upper layer 10c on the intermediate layer 10b. The lower layer 10a is formed into a strip (band) form of a predetermined width W including a center portion of a liquid absorbing region of the disposable diaper. The intermediate layer 10b has a smaller width than the lower layer 10a. The upper layer 10c is formed to have a further smaller width than the intermediate layer 10b.

The intermediate layer 10b is located at the center portion of the lower layer 10a. The upper layer 10c is located at the center portion of the intermediate layer 10b. Therefore, the surface structural body 10 is so protruded at the center portion thereof that the basis weight and bulkiness are smaller at laterally opposite side portions, and are increased toward the center portion.

The lower layer 10a is a bundle of continuous filaments 11a. Similarly, the intermediate layer 10b and the upper layer 10c are also a bundle of continuous filaments 11b and a bundle of continuous filaments 11c, respectively. These individual continuous filaments 11a, 11b and 11c extend in the Y direction over the entire length of the surface structural body 10 without interruption.

Each of the layers 10a, 10b and 10c is prepared by opening a filament bundle (called as "tow"), in which crimped continuous filaments (11a, 11b or 11c) are bundled. By opening process, individual continuous filaments forming each tow are separated from each other and spread in a width direction of the tow to provide a uniform bulkiness, for forming the lower layer 10a, the intermediate layer 10b and the upper layer 10c.

The continuous filaments 11a, 11b and 11c are formed of a heat-fusible, hydrophobic synthetic resin. For example, the continuous filaments 11a, 11b and 11c may be conjugated synthetic fibers of core-sheath structure, such as those of PE/PET, PE/PP or the like, side-by-side type conjugated fibers, such as those of PE/PET, PE/PP or the like, or mono fibers, such as those of PE, PP, PET or the like. It is also preferred that the continuous filaments 11a, 11b and 11c contain inorganic filler for whitening, such as titanium oxide or the like, in the content of 0.5 to 10% by weight. By whitening process, the urine absorbed in the absorbent core 8 can be easily concealed from external view. The individual continuous filaments may have a circular or modified cross-section.

Crimping is provided for the continuous filaments upon production by means of crimper and number of crimp is increased by pre-heating calender or hot air treatment. In the alternative, through pre-heating calender, drawing and relaxing are repeated to cause strain in orientation of resin forming the continuous filaments to cause crimp in coil form.

Opening of a bundle of crimped continuous filaments can be performed as following. While the bundle is transported between transporting rolls, tension force is applied in the direction along which the filaments extend, and then the tension force is released. These processes are repeated to separate individual continuous filaments from each other for opening. In the alternative, it is also possible to perform opening of the bundle by urging sliding plates onto the bundle from opposite sides. In this method, the bundle transported between transporting rolls is slidingly contacted with the sliding plates, and individual filaments are separated from each other by sliding contact force for opening. The latter method employing the sliding plates has been disclosed in commonly owned co-pending U.S. Patent Application for "METHOD AND APPARATUS FOR OPENING CONTINUOUS FILAMENTS" (claiming priority based on Japanese Patent Application No.2000-265458). The disclosure of the above-identified commonly owned co-pending U.S. Patent Application is herein incorporated by reference. The bundle of continuous filaments thus opened has a small filament density and a large apparent width.

Furthermore, the opened filament bundle is subjected to a spreading (widening) process to be spread (widened) in the width direction to have a predetermined width. Thus, there are formed the lower layer 10a of the width W, and the intermediate and upper layers 10b and 10c of widths smaller than the width W of the lower layer 10a.

On the bundle of the opened and spread continuous filaments 11a for forming the lower layer 10a, the bundle of the continuous filaments 11b for forming the intermediate layer 10b and the bundle of the continuous filaments 11c for forming the upper layer 10c are stacked. Fixing lines 12 are formed by means of welding rolls, at least one of which contains a pattern of protrusions for embossing on the peripheral surface. At respective fixing lines 12, the continuous filaments 11a of the lower layer 10a, the continuous filaments 11b of the intermediate layer 10b, and the continuous filaments 11c of the upper layer 10c are heat fused or welded by induction heating with ultrasonic wave to thereby form into a sheet.

As shown in FIGS. 1 and 3, each fixing line 12 extends in straight in the X direction. The fixing lines 12 are spaced apart from each other in the Y direction by a predetermined pitch P. However, fixing lines should not be limited to the shown straight-line shape but may extend in various forms, for example, in the form of continuous line approximated to trigonometric curve or V-shaped line. It is also possible to provide a plurality of short fixing lines intermittently arranged at a given interval in the X direction, so long as consideration is given to prevention of falling out of filaments. Various alternation of the short fixing line patterns are disclosed in commonly owned co-pending U.S. patent application, for "ABSORBENT ARTICLE EMPLOYING SURFACE LAYER WITH CONTINUOUS FILAMENT AND MANUFACTURING PROCESS THEREOF" (claiming priority based on Japanese Patent Application No. 2000-265467). The disclosure of the above-identified commonly owned co-pending U.S. patent application will be herein incorporated by reference. Of course, it is possible to replace the short fixing lines with circular dot-shaped fixing portions or the like.

The surface structural body 10 can be easily manufactured by the foregoing process of feeding and stacking the bundles of the continuous filaments for forming the lower layer 10a, the intermediate layer 10b and the upper layer 10c, and fixing the bundles by means of welding rolls. In this manufacturing process, moreover, the widths, basis weights and bulkinesses of respective layers can be freely varied. In the shown embodiment, the surface structural body 10 has three layers. However, the number of layers should not be limited to three. For example, the surface structural body may have two layers only of a lower layer and an upper layer, or may have multilayer structure of four or more layers.

As shown in FIG. 3, the single-layer portion which consists of the lower layer 10a has a thickness T1, the two-layered portion where the lower layer 10a and the intermediate layer 10b are stacked has a thickness T2, and the three-layered center portion where the lower layer 10a, the intermediate layer 10b and the upper layer 10c are stacked has a thickness T3. Thus, the surface structural body 10 has different thicknesses and basis weights at the respective portions in the width direction (X direction).

For example, the thickness T1 is in a range of 5 to 8 mm, the thickness T2 is in a range of 8 to 15 mm, and the thickness T3 is in a range of 15 to 25 mm. The basis weight of the single-layer portion of the thickness T1 is in a range of 25 to 75 g/m$^2$, the basis weight of the two-layered portion of the thickness T2 is in a range of 75 to 100 g/m$^2$ and the basis weight of the three-layered portion of the thickness T3 is in a range of 100 to 200 g/m$^2$.

On the other hand, an average filament density of the entire surface structural body 10 including the lower layer 10a, the intermediate layer 10b and the upper layer 10c is in a range of 0.002 to 0.01 g/cm$^3$.

The finenesses of the continuous filaments 11a, 11b and 11c forming the respective layers are in a range of 1.1 to 20 dtex, and preferably in a range of 1.1 to 11 dtex.

In the individual continuous filaments 11a, 11b and 11c, number of crimp is in a range of 5 to 30 per inch, and preferably in a range of 15 to 30, and crimp modulus of elasticity is preferably greater than or equal to 70%.

Number of crimp is based on JIS L-1015 and crimp modulus of elasticity is based on JIS L-1074. In case of the filament of a fineness less than 5.5 dtex, an initial load of 0.49 mN is applied in pulling direction, and in case of the filament of a fineness greater than or equal to 5.5 dtex, an initial load of 0.98 mN is applied in pulling direction. Number of crimp referred to is number of threads (peaks) per 1 inch (25 mm) when the initial load is applied.

On the other hand, the crimp modulus of elasticity is expressed by:

$$\{(b-c)/(b-a)\} \times 100 \ (\%)$$

wherein a is a length of filament when the initial load is applied, b is a length when the crimp is stretched by applying a tension force of 4.9 mN per 1.1 dtex for 30 seconds, and c is a length as applied the initial load again after 2 minutes from releasing the tension force.

In the disposable diaper 1 employing the surface structural body 10, since the portion for directly contacting with the wearer's skin is formed with the continuous filaments, no fiber end appears on the surface thereof. Therefore, the surface structural body provides smooth contact feeling on the skin. Furthermore, since the continuous filaments can move relatively freely to follow movement of the wearer's skin, the surface structural body becomes less irritative to the skin. Also, the surface structural body is so bulky as to provide superior cushioning ability.

As shown in FIGS. 2 and 3, the surface structural body 10 has the largest thickness T3 at the center portion. Therefore, when used for lady or girl, the surface structural body 10 can be easily fitted on the discharge region of the wearer, at the center portion of the thickness T3. Accordingly, the liquid such as urine discharged from the discharge region of the wearer is immediately applied to the upper layer 10c tightly fitted thereon, so that the liquid may pass through the surface structural body 10 without causing lateral spread, to be absorbed in the absorbent core 8. In short, since the surface structural body 10 can be easily fitted on the wearer's discharge region and a gap between the discharge region and the surface structural body 10 is hardly formed, lateral leakage of liquid such as urine can be successfully prevented.

Furthermore, since the continuous filaments 11a, 11b and 11c extend in the longitudinal direction (Y direction) of the disposable diaper 1, the liquid is preferentially guided in the longitudinal direction to thereby prevent lateral leakage in the width direction (X direction). Here, since the continuous filaments 11a, 11b and 11c are fixed at the fixing lines 12 spaced apart in the longitudinal direction by the given pitch P, spreading of the liquid in the longitudinal direction in the surface structural body 10 can be restricted to facilitate guiding of the liquid to the absorbent core 8.

In the surface structural body 10, hydrophilicity of continuous filaments may be different for different layers, for example, such that hydrophilicity of the lower layer 10a is higher than that of the upper layer 10c, or such that hydrophilicity is increased in the order from the upper layer 10c to the lower layer 10a (i.e., hydrophilicities of the upper layer 10c, the intermediate layer 10b and the lower layer 10a are varied in ascending order from the upper layer 10c to the lower layer 10a). Alternatively, filament density may be different for different layers, for example, such that filament density of the upper layer 10c is higher than that of the lower layer 10a, or such that filament density of the lower layer 10a is higher than that of the upper layer 10c. Of course, it is also possible that both hydrophilicity and density are different for different layers.

For example, if hydrophilicity is increased toward the lower layer 10a, the liquid such as urine applied to the upper layer 10c is drawn to the continuous filaments of the underlying layers to be easily guided to the absorbent core 8. It this case, moreover, since hydrophilicity is decreased toward the upper layer 10c (preferably, the upper layer 10c is hydrophobic), the liquid such as urine once absorbed by the absorbent core 8 can be effectively prevented from flowing back toward the wearer's skin. Similarly, if density is increased toward the lower layer 10a, the liquid such as urine applied to the upper layer 10c is drawn by capillary effect of the higher density layer to achieve superior liquid permeability to the absorbent core 8. Also, flowing back of liquid such as urine toward the wearer's skin can be successfully prevented.

Here, a difference in hydrophilicity represents a difference in interfacial chemical nature on the filament surface, and hydrophilicity becomes higher at lower contact angle of water, in case of hydrophobic filament.

In this embodiment, as set forth, the continuous filaments are hydrophobic filaments, such as core-sheath type conjugated fibers of PE/PP or PE/PET. In the case where these hydrophobic continuous filaments are treated to be hydrophilic by applying a hydrophilic oil solution onto the surfaces of the continuous filaments, a difference in hydrophilicity can be provided by using hydrophilic oil solutions having different durabilities against liquid.

For example, onto the continuous filaments of the upper layer 10c and/or the intermediate layer 10b, applied is an initial hydrophilic oil solution, namely a hydrophilic oil solution which can relatively easily drop off as contacting with water or other liquid. This kind of initial hydrophilic oil solution may be PEG modified polyester, polyoxyethylene alkyl sulfate, alkyl phosphoric ester K salt, polyoxyethylene alkyl ester, alkylsulfonate Na salt and so forth.

On the other hand, onto the continuous filaments of the lower layer 10a, applied is a durable hydrophilic oil solution which is difficult to drop off by water or other liquid in comparison with the initial hydrophilic oil solution. The durable hydrophilic oil solution may be polyether ester, ether nonion, polyether modified silicon, sulfo succinate, polyoxyethylene amide ether, alkyl imidazoline type cation, polyglycerol polyester and so forth.

With the hydrophilic oil solutions being thus selected to make the durability of hydrophilic oil solution against liquid higher in the lower layer 10a, the lower layer 10a is permitted to have a higher hydrophilicity than those of the upper and intermediate layers 10c and 10b. In case where the upper layer 10c is formed of the hydrophobic continuous filaments without hydrophilic treatment, the initial hydrophilic oil solution is applied to the continuous filaments of the intermediate layer 10b, and the durable hydrophilic oil solution is applied to the continuous filaments of the lower layer 10a, hydrophilicity can be increased in the order from the upper layer 10c to the lower layer 10a.

In an alternative, a difference in hydrophilicity may be provided by varying application amount of the hydrophilic oil solution per unit fineness (1 dtex) of the continuous filaments of the upper, intermediate and lower layers 10c, 10b and 10a. For example, hydrophilicity may be increased in the order from the upper layer 10c to the lower layer 10a, by applying no hydrophilic oil solution to the continuous filaments 11c of the upper layer 10c, by applying small amount of hydrophilic oil solution to the continuous filaments 11b of the intermediate layer 10b, and by applying greater amount of hydrophilic oil solution to the continuous filaments 11a of the lower layer 10a.

It is also possible to provide a difference in hydrophilicity by utilizing hydrophilic fibers. Hydrophilic fibers can draw moisture by hydrophilic group on the surface thereof. Here, examples of the hydrophilic fibers include hydrophilic continuous filaments, such as those of cellulose acetate, and hydrophilic short fibers, such as natural cellulose fibers. For example, hydrophilicity may be increased in the order from the upper layer 10c to the lower layer 10a, by forming the upper layer 10c with the hydrophobic continuous filaments not processed by hydrophilic treatment, by forming the intermediate layer 10b with the hydrophobic continuous filaments treated to be hydrophilic, and by forming the lower layer 10a with the hydrophilic continuous filaments, such as those of cellulose acetate. On the other hand, the hydrophilic short fibers, such as natural cellulose fibers, may be bonded to the hydrophobic continuous filaments of the lower layer 10a with an adhesive or the like, for enhancing hydrophilicity of the lower layer 10a.

Next, a difference in density can be adjusted by varying the fineness of the continuous filaments. For example, by employing continuous filaments of a smaller fineness, the filament density can be made higher. By varying the fineness, it is possible to make the density of the lower layer 10a higher than that of the upper layer 10c or to increase the density in the order from the upper layer 10c to the lower layer 10a.

On the other hand, by varying number of crimp of the continuous filaments and/or elastic modulus of crimp of the continuous filaments, a difference in density can be provided between the layers. For example, density can be made higher by increasing number of crimp of the continuous filaments. On the other hand, by increasing the elastic modulus of crimp, density can be lowered.

FIG. 4 is a section of a disposable diaper 1A according to a second embodiment of the present invention, in which a surface structural body 20 shown in FIG. 5 is used in place of the surface structural body 10 shown in FIG. 3. Except for the surface structural body 20, the disposable diaper 1A has the same structure as that of the disposable diaper 1.

In the shown embodiment, the surface structural body 20 is formed by stacking a lower layer 20a, an intermediate layer 20b and an upper layer 20c. Each of the layers 20a, 20b and 20c is prepared in the same manner as in the first embodiment by opening a filament bundle (called as "tow"), in which crimped continuous filaments (21a, 21b or 21c) are bundled. That is, the layers 20a, 20b and 20c are formed of opened continuous filaments 21a, 21b and 21c, respectively, to have a predetermined uniform bulkiness. The individual continuous filaments 21a, 21b and 21c extend in the Y direction over the entire length of the surface structural body 20 without interruption.

In the shown embodiment, however, the intermediate layer 20b and the upper layer 20c are individually formed into two parallel strips (bands) which are located on laterally opposite side portions of the lower layer 20a to exposed the center portion of the lower layer 20a. Here, the width of the lower layer 20a is larger than the width of the intermediate layer 20b (i.e., the total width of the two strips of the intermediate layer 20b), and the width of the intermediate layer 20b is larger than the width of the upper layer 20c (i.e., the total width of the two strips of the upper layer 20c). The individual continuous filaments forming the lower layer 20a, the intermediate layer 20b and the upper layer 20c are fusion bonded to each other at fixing lines 22 which are spaced apart from each other in the Y direction by a given pitch P.

Thus, as shown in FIG. 5, the surface structural body 20 has three portions including single-layer center portion of a thickness T1, two-layered portion of a thickness T2 outside of the single-layer center portion, and three-layered portion of a thickness T3 outside of the two-layered portion. The thicknesses T1, T2 and T3 and the basis weights of respective portions are the same as those in the surface structural body 10 shown in FIG. 3. Also, the fineness of the continuous filaments and the average filament density of the entire surface structural body 20 are the same as those in the surface structural body 10.

The disposable diaper 1A shown in FIG. 4 is particularly suited for gentle man or boy since the surface structural body 20 having high bulkiness at laterally opposite sides is used. Furthermore, since the surface structural body 20 has large bulkiness at laterally opposite sides where the intermediate layer 20b and the upper layer 20c are located, the intermediate layer 20b and the upper layer 20c substantially serve as leakage preventing banks for preventing lateral leakage of urine.

Of course, similarly to the surface structural body 10 shown in FIG. 3, the surface structural body 20 may also have a difference in hydrophilicity and/or filament density between layers. For example, hydrophilicity and/or filament density of the lower layer 20a may be higher than that of the upper layer 20c, or, hydrophilicity and/or filament density may be increased in the order from the upper layer 20c to the lower layer 20a.

In order to enhance leakage preventing effect, on the other hand, it may be possible to provide higher density for the upper layer 20c than that of the lower layer 20a. It is also possible to increase density in the order from the lower layer 20a to the upper layer 20c. In the alternative, it is possible to use hydrophobic continuous filaments treated to be hydrophilic as the continuous filaments 21a of the lower layer 20a and to subject at least one of the intermediate layer 20b and the upper layer 20c to water-repelling treatment, for enhancing function as the leakage preventing banks for preventing lateral leakage of urine or the like.

In the embodiment shown in FIGS. 4 and 5, the leakage preventing banks can be formed by stacking the bundles of the opened continuous filaments 21b and 21c (i.e., the intermediate and upper layers 20b and 20c) on the bundle of the opened continuous filaments 21a (i.e., the lower layer 20a) and partially fusion bonding them. In comparison with conventional leakage preventing walls each composed of a hydrophobic sheet and an elastic member, these leakage preventing banks can be formed simply.

As has been described above, the surface structural bodies 10 and 20 shown in FIGS. 3 and 5 have three-layered structure. However, it should be noted that the intermediate layers 10b and 20b may be omitted from the surface structural bodies 10 and 20 to provide two-layered structure formed only of the lower and upper layers 10a and 10c and the lower and upper layers 20a and 20c, respectively.

Figure 6:
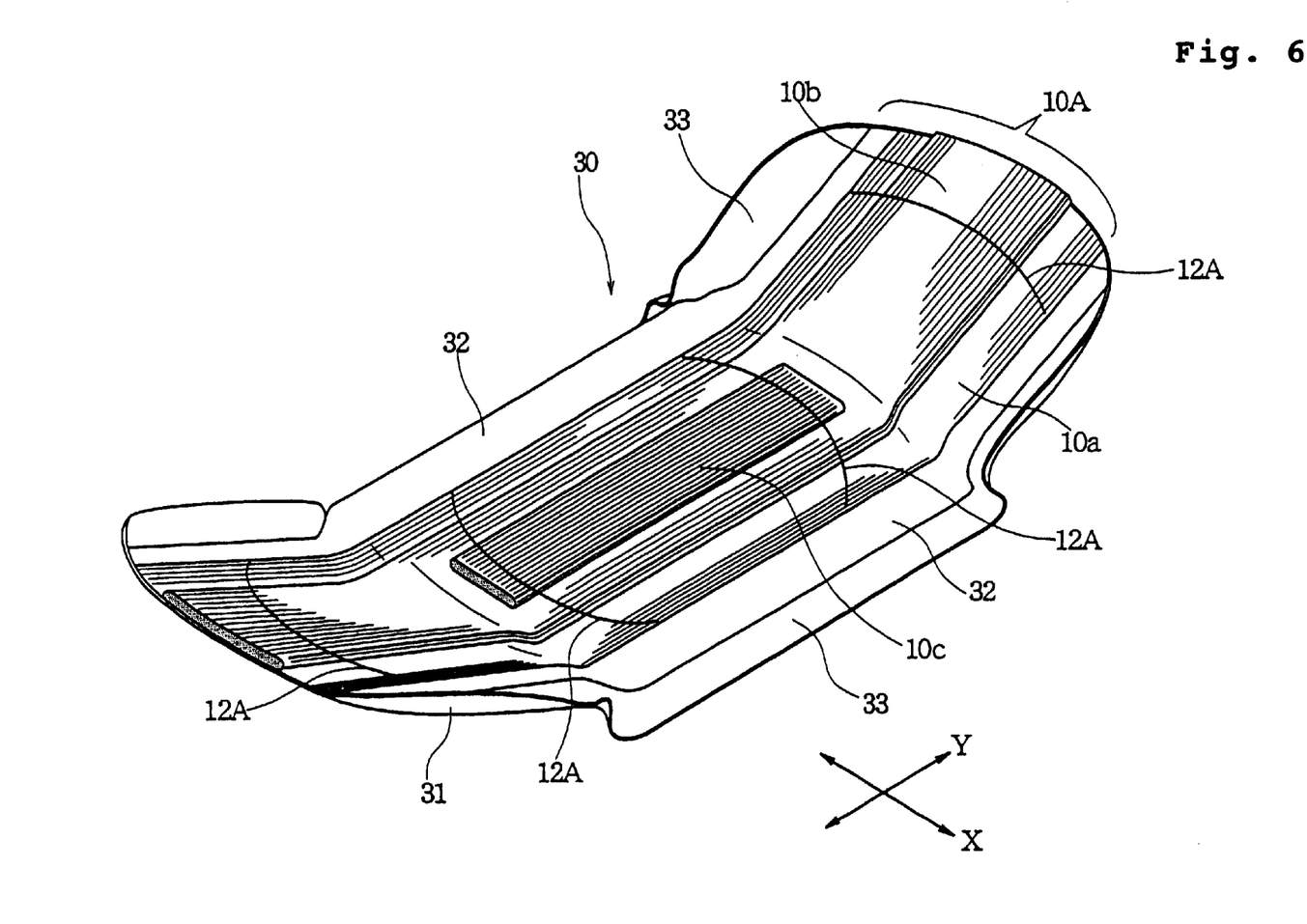
FIG. 6 is a perspective view showing a sanitary napkin as an absorbent article according to a third embodiment of the invention.

FIG. 6 is a perspective view showing a sanitary napkin 30 as an absorbent article according to a third embodiment of the present invention.

In the sanitary napkin 30, an absorbent core is provided on a liquid impermeable backing sheet 31, and on the absorbent core, provided is a surface structural body 10A having construction similar to that of the surface structural body 10 shown in FIG. 3. At laterally opposite sides of the sanitary napkin 30, moreover, provided are leakage preventing walls 32 and 32 formed with hydrophobic sheets. These hydrophobic sheets are joined to the backing sheet 31 at laterally opposite flap portions 33 and 33.

The surface structural body 10A of the sanitary napkin 30 is constructed to include lower, intermediate and upper layers of continuous filament bundles, which are stacked in the same manner as in the surface structural body 10 shown in FIG. 3 and therefore designated by the common reference numerals 10a, 10b and 10c, except that the upper layer 10c is located at the longitudinal center portion of the sanitary napkin (i.e., except that the upper layer 10c does not extend over the entire length of the surface structural body).

The individual continuous filaments of the lower layer 10a, the intermediate layer 10b and the upper layer 10c are partially fusion bonded at fixing lines 12A of curved line shape to be formed into a sheet form. In the surface structural body 10A, since the center portion is bulged, the bulged center portion may be firmly fitted on the discharge region of the wearer to facilitate prevention of lateral leakage of menstrual blood.

Also in the surface structural body 10A, hydrophilicity and/or density may be increased in the order from the upper layer 10c to the lower layer 10a, for improving liquid permeability and for preventing flowing back of liquid. It is also possible to form the surface structural body 10A only with two layers of the lower layer 10a and the upper layer 10c.

On the other hand, while the surface structural body is formed only with the bundles of the continuous filaments in the foregoing embodiments, the surface structural body may further comprise a liquid permeable non-woven fabric sheet, which is provided below and joined to the bundles of the continuous filaments forming the foregoing layers.

As set forth, in the present invention, the surface structural body of the absorbent article may be provided good liquid permeability with successfully preventing flowing back of the liquid. Furthermore, the absorbent article may have superior cushioning ability for providing soft contact feeling to the wearer's skin. This surface structural body with difference bulkinesses (more preferably with different hydrophilicities and densities) can be manufactured through simple process of stacking the bundles of the continuous filaments into a plurality of layers.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

For instance, the layer of the continuous filaments may also be applicable for the back side of the backing sheet to be exposed externally. Such application has been disclosed in commonly owned co-pending U.S. Patent Application, for "ABSORBENT ARTICLE WITH BACKING SHEET HAVING CONTINUOUS FILAMENTS" (claiming priority based on Japanese Patent Application No. 2000-265527). The disclosure of the above-identified co-pending U.S. Patent Application is herein incorporated by reference. Also, structure shown in the commonly owned co-pending U.S. Patent Application, for "ABSORBENT ARTICLE WITH SURFACE MEMBER OF CONTINUOUS FILAMENTS" (claiming priority based on Japanese Patent Application No. 2000-265496) is applicable for the present invention. The disclosure of the above-identified co-pending U.S. Patent Application is herein incorporated by reference.

What is claimed is:

1. An absorbent article comprising:

a liquid permeable surface structural body;

a backing sheet;

an absorbent core disposed between said surface structural body and said backing sheet, said surface structural body including a lower layer adjacent to said absorbent core, an upper layer away from said absorbent core, and an intermediate layer between said lower layer and said upper layer, widths of said lower layer, said intermediate layer and said upper layer being varied in descending order from said lower layer to said upper layer so that said upper layer is located exclusively over a center portion of said lower layer or two separate portions of said upper layer are located exclusively over laterally opposed side portions of said lower layer, each layer being a bundle of continuous filaments individually extending over an entire length thereof, said continuous filaments of respective layers being partially fixed together, wherein hydrophilicities of said upper layer, said intermediate layer and said lower layer are varied in ascending order from said upper layer to said lower layer.

2. The absorbent article as set forth in claim 1, wherein said upper layer is formed of hydrophobic continuous filaments not subjected to hydrophilic treatment.

3. The absorbent article as set forth in claim 1, wherein said lower layer, said intermediate layer and said upper layer have different filament densities.

4. The absorbent article as set forth in claim 3, wherein filament densities of said lower layer, said intermediate layer and said upper layer are varied in ascending order from said upper layer to said lower layer.

* * * * *